US00RE36130E

United States Patent [19]

Haynes

[11] E Patent Number: Re. 36,130

[45] Reissued Date of Patent: Mar. 9, 1999

[54] ULTRASONIC THICKNESS GAGE FOR PIPE

[75] Inventor: John Haynes, Houston, Tex.

[73] Assignee: ICO, Inc., Houston, Tex.

[21] Appl. No.: 650,953

[22] Filed: May 20, 1996

Related U.S. Patent Documents

Reissue of:

[64] Patent No.: 5,313,837
Issued: May 24, 1994
Appl. No.: 766,645
Filed: Sep. 26, 1991

[51] Int. Cl.[6] ..... G01N 29/10; G01N 29/26

[52] U.S. Cl. ..... 73/622; 73/634; 73/640

[58] Field of Search ..... 73/620, 621, 622, 73/633, 640, 644, 634

[56] References Cited

U.S. PATENT DOCUMENTS

| | | | |
|---|---|---|---|
| 3,375,706 | 4/1968 | Pandelis et al. | 73/622 |
| 3,616,684 | 11/1971 | Nusbickel, Jr. | 73/635 |
| 3,631,714 | 1/1972 | Cressman et al. | 73/644 |
| 3,771,354 | 11/1973 | Miller | 73/639 |
| 3,777,552 | 12/1973 | Fletcher et al. | 73/622 |
| 3,777,554 | 12/1973 | Papay et al. | 73/637 |
| 3,791,199 | 2/1974 | Toth et al. | 73/609 |
| 3,798,961 | 3/1974 | Flambard et al. | 73/644 |
| 3,916,676 | 11/1975 | Boggs et al. | 73/622 |
| 3,958,451 | 5/1976 | Richardson | 73/644 |
| 4,041,773 | 8/1977 | Hauldren et al. | 73/623 |
| 4,106,347 | 8/1978 | DeKerlegand | 73/622 |
| 4,143,554 | 3/1979 | Nagy et al. | 73/641 |
| 4,217,782 | 8/1980 | Pont | 73/637 |
| 4,261,034 | 4/1981 | Saccomano et al. | 364/200 |
| 4,262,331 | 4/1981 | Freeland et al. | 364/200 |
| 4,328,708 | 5/1982 | Bagwell | 73/622 |
| 4,331,034 | 5/1982 | Takeda et al. | 73/637 |
| 4,375,165 | 3/1983 | de Sterke | 73/622 |
| 4,404,853 | 9/1983 | Livingston | 73/622 |
| 4,475,399 | 10/1984 | Livingston | 73/622 |
| 4,487,072 | 12/1984 | Livingston | 73/622 |
| 4,531,413 | 7/1985 | Tsuchita et al. | 73/637 |
| 4,541,064 | 9/1985 | Livingston | 364/552 |
| 4,562,738 | 1/1986 | Nakayma et al. | 73/622 |
| 4,567,747 | 2/1986 | Matay | 73/622 |
| 4,586,379 | 5/1986 | Burkhardt, Jr. | 73/622 |
| 4,596,953 | 6/1986 | Nagasaka et al. | 73/622 |
| 4,660,419 | 4/1987 | Derkacs et al. | 73/622 |
| 4,672,852 | 6/1987 | Gugel et al. | 73/622 |
| 4,718,277 | 1/1988 | Glascock | 73/622 |
| 4,843,884 | 7/1989 | House et al. | 73/622 |
| 5,007,291 | 4/1991 | Walters et al. | 73/622 |
| 5,079,952 | 1/1992 | Nakaso et al. | 73/624 |

FOREIGN PATENT DOCUMENTS

| | | |
|---|---|---|
| 1400484 | 9/1965 | France . |
| 28 06 550 | 8/1979 | Germany . |
| 52 53486 | 4/1977 | Japan . |

*Primary Examiner*—Hezron E. Williams
*Assistant Examiner*—Rose M. Miller
*Attorney, Agent, or Firm*—Browning Bushman

[57] ABSTRACT

The invention is a compact ultrasonic tester involving rotating sensors The processor rotates with the sensors so that the output signal of the processor goes through the slip rings, rather than the output signal of the sensors. A spraying system is incorporated in conjunction with rollers. The rollers take the applied spray on the pipe surface and paint a film on the outer pipe surface to allow a good contact for meaningful results. A floating shoe is provided for holding each sensor against the pipe wall. The sensors are biased into contact with the pipe surface and the machine can handle different diameters of pipe. By controlling the pipe speed of advance and the rotational speed or the sensors, 100 percent coverage of the pipe wall is assured. The machine is compact and can be installed behind existing electromagnetic/gamma testers without major modifications to pipe-testing facilities.

43 Claims, 4 Drawing Sheets

ULTRASONIC THICKNESS GAGE FOR PIPE

Matter enclosed in heavy brackets [ ] appears in the original patent but forms no part of this reissue specification; matter printed in italics indicates the additions made by reissue.

FIELD OF THE INVENTION

The field of this invention is a machine that ultrasonically tests pipe.

BACKGROUND OF THE INVENTION

In the past, machines that were used to inspect pipes used electromagnetic waves to detect transverse and longitudinal faults. Also combined as a feature in such machines was the use of gamma rays to detect wall thickness. Pipes were fed into these machines and rotated as they were being fed. However, the downside of this type of inspection is that it missed about 70 percent of the pipe wall area. Furthermore, the wall thickness test involved an averaging of a measurement of two opposing walls; therefore, a complete picture of the wall thickness at the point of inspection was not clearly known.

More recently, ultrasonic testing machines have been developed. Some of these use a plurality of ultrasonic sensors which are fixedly mounted while the pipe is rotated and advanced over the sensors. The sensors provide information on the pipe condition, including defects as well as wall thickness. The problem with such machines is that they require so many sensors and complex computer equipment to analyze all of the signals obtained from the sensors on a real-time basis, that inspection using such machines proves to be a very costly endeavor. Using the stationary multiple sensors as just described results in a charge to the customer of approximately 4–6 times as much as pipe inspected using the older technology involving electromagnetic waves.

There have also been machines that use ultrasonic technology where the sensors themselves spin around the pipe. Typically, these sensors generate a high-frequency, low-voltage signal which must go through a slip ring because the sensors themselves are rotated around the pipe. The signal, after going through the slip ring, goes to a processor which converts the information to a useful form with regard to imperfections in the pipe. The problems associated with machines of this design is that the high-frequency, low-voltage signal going through the slip ring was subject to interference which resulted in affecting the signal accuracy transmitted from the sensor to the processor.

The apparatus of the present invention exhibits a marked improvement from known ultrasonic sensors in that the processor rotates about the pipe with the sensors, and the signal going through the slip ring is the output from the processor. Therefore, the signal generated by the processor which is low-frequency and high-voltage is not as easily subject to interference as the high-frequency, low-voltage signals put through the slip rings in the prior designs.

Another problem exhibited by ultrasonic testing machines is the need to get good contact at the surface to obtain the readings. The apparatus of the present invention has incorporated a sprayer/roller combination which in effect paints a liquid surface on the pipe as it advances toward the sensors. The sprayers in combination with the rollers spread a film over the outer surface of the pipe to facilitate getting a good contact between the sensor holder and the pipe so that accurate readings can be obtained. This feature, in combination with a floating shoe for the sensor, improves accuracy due to better contact with the pipe wall.

Another feature of the apparatus of the present invention is its compactness which allows it to be added to an existing testing facility which employs a combination of electromagnetic and gamma rays to test pipe. Thus, what results is a combination of machines that when put together allow tests to be done economically yet greatly improve the coverage problems associated with using the electromagnetic waves/gamma ray technology to test pipe. By controlling the advance speed of the pipe, as well as the rotational speed of the sensors, coverage over 100 percent of the pipe area can be assured.

Of interest as far as the state of the prior art are U.S. Pat. Nos. 5,007,291; 4,562,738; 4,843,884; 4,328,708; 4,596,953; and 4,672,852; all of which illustrate ultrasonic testing machines with rotating sensors in combination with the use of slip rings and an applied liquid. Several ultrasonic testers are portable for use on existing pipes, such as U.S. Pat. Nos. 4,331,034 and 4,531,413 and 4,586,379. Other testers employ stationary probes such as U.S. Pat. Nos. 4,718,277; 4,660,419; 4,567,747; and 4,475,399.

SUMMARY OF THE INVENTION

The invention is a compact ultrasonic tester involving rotating sensors. The processor rotates with the sensors so that the output signal of the processor goes through the slip rings, rather than the output signal of the sensors. A spraying system is incorporated in conjunction with rollers. The rollers take the applied spray on the pipe surface and paint a film on the outer pipe surface to allow a good contact for meaningful results. A floating shoe is provided for holding each sensor against the pipe wall. The sensors are biased into contact with the pipe surface and the machine can handle different diameters of pipe. By controlling the pipe speed of advance and the rotational speed of the sensors, 100 percent coverage of the pipe wall is assured. The machine is compact and can be installed behind existing electromagnetic/gamma testers without major modifications to pipe-testing facilities.

DETAILED DESCRIPTION OF THE PREFERRED EMBODIMENT

Figure 1:
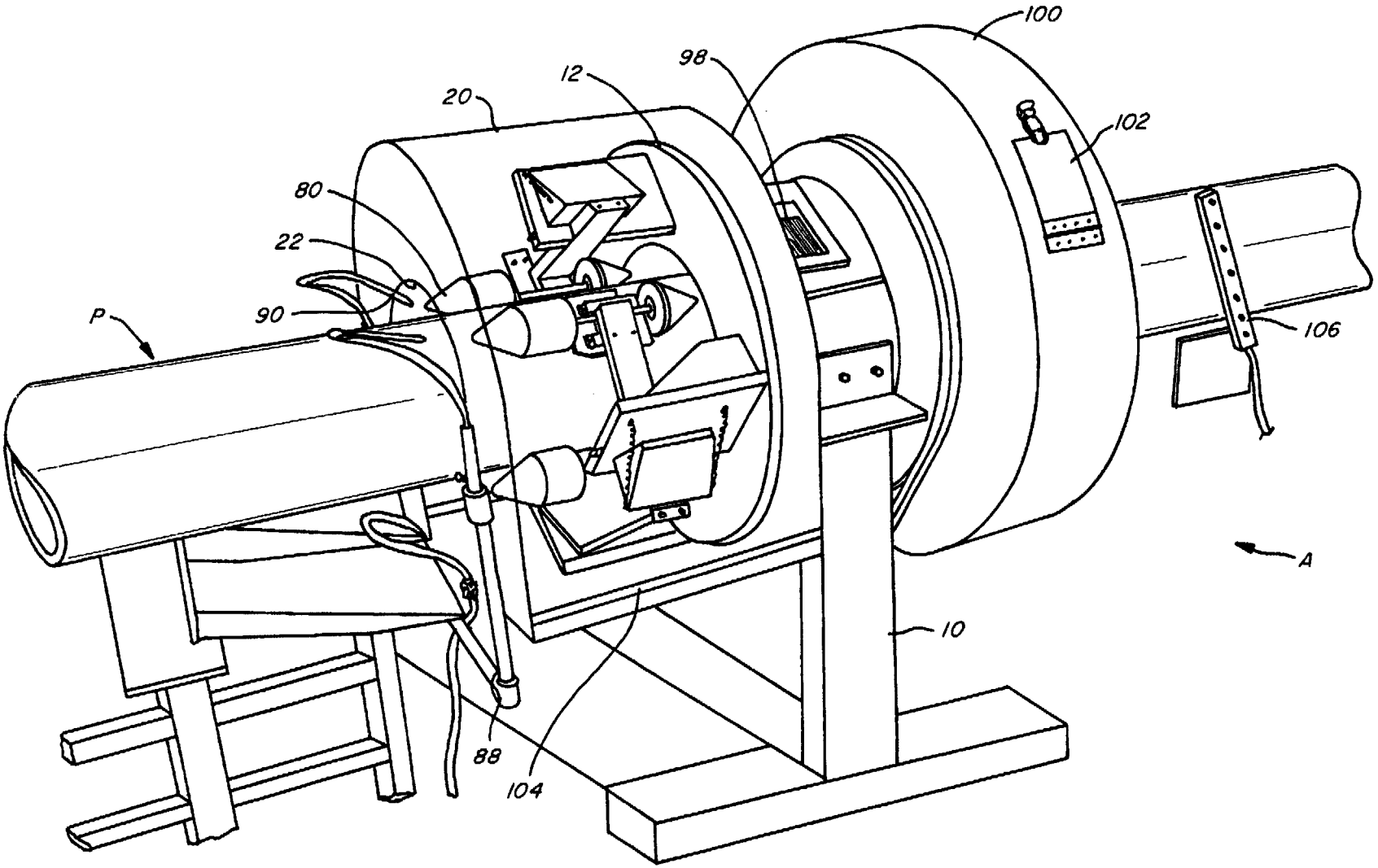
FIG. 1 is a perspective view of the machine with a pipe mounted in it, being tested.

The apparatus A is illustrated in FIG. 1. It comprises of a frame 10 upon which is supported drum 12 (see FIG. 2). A motor 14 is connected to drum 12 via drive belt 16. Idler 18 is adjustably mounted to take the slack out of belt 16. Drum 12 rolls on a bearing (not shown) that is mounted to it. Mounted over drum 12 is a hood 20. The hood 20 has a cutout 22 at the inlet end of the apparatus A. The pipe P is moved by conventional means into alignment with opening 22 and advanced along its axis through the apparatus A. Note that the apparatus A does not require the pipe P to be rotated as it is advanced through the apparatus A. Instead, drum 12 is driven by motor 14, which in turn moves the ultrasonic sensors.

Figure 2:
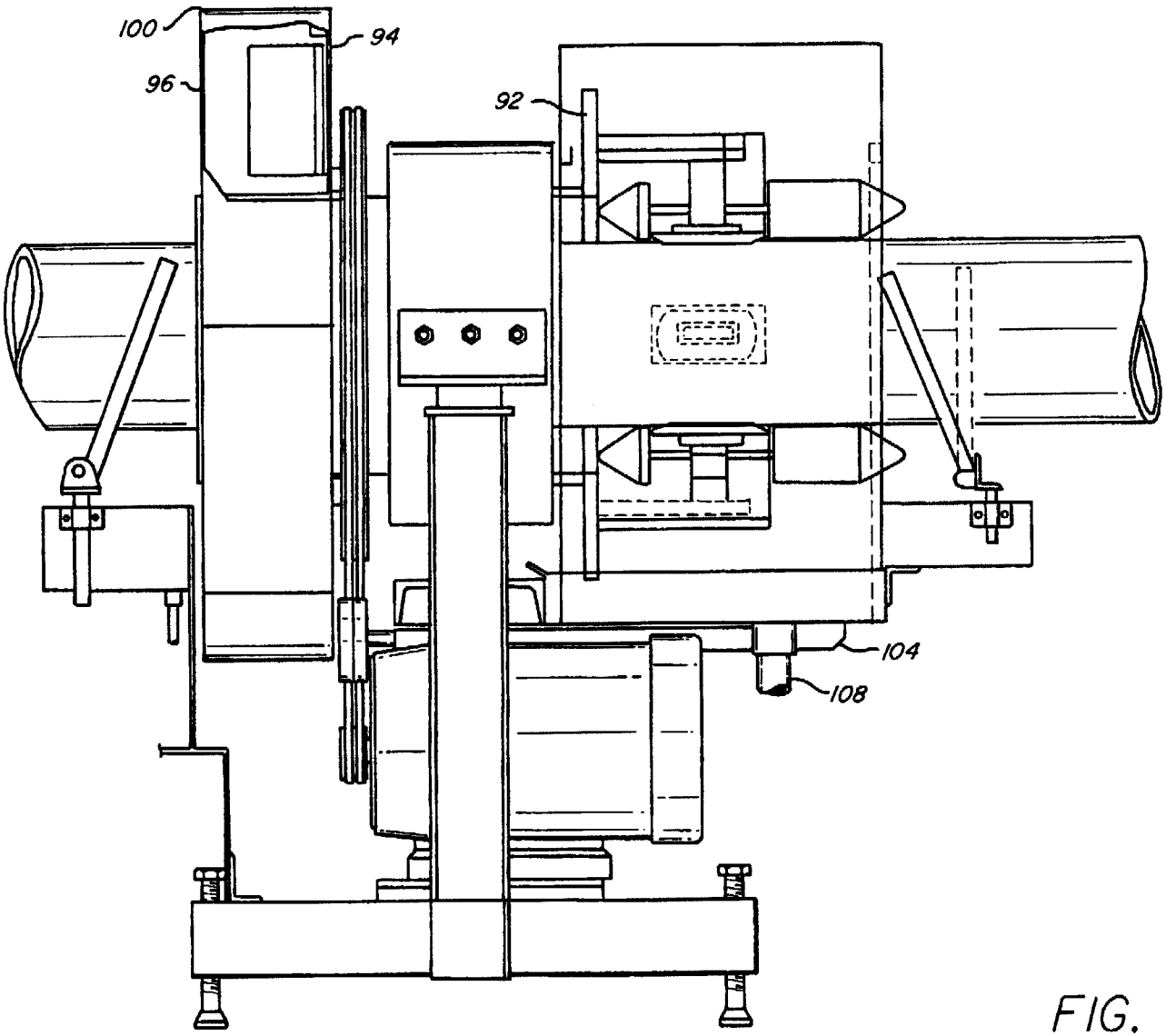
FIG. 2 is a side view of the machine shown in FIG. 1.
Figure 3:
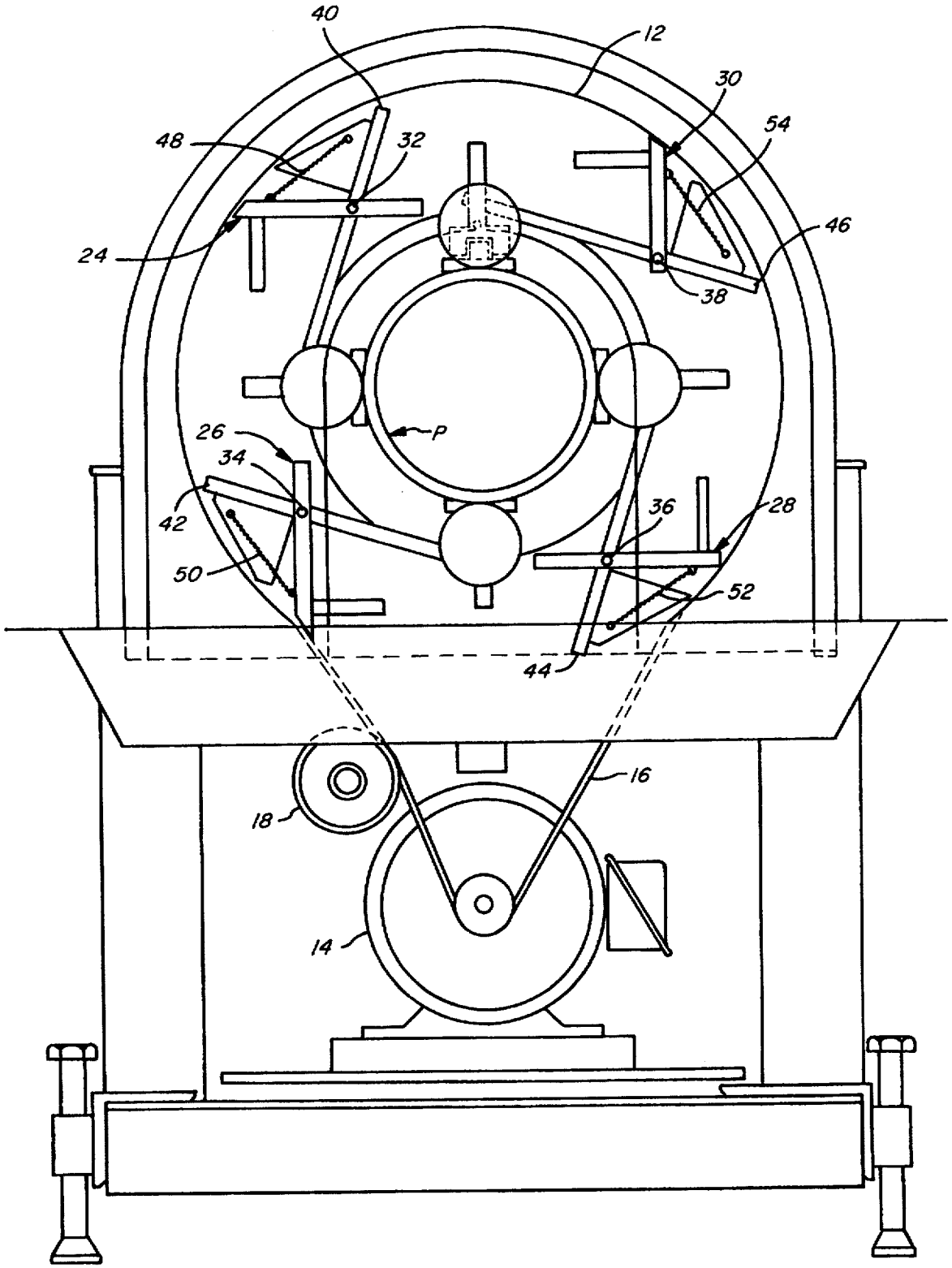
FIG. 3 is an end view of the machine shown in FIG. 1, as seen from the inlet end of the machine.
Figure 4:
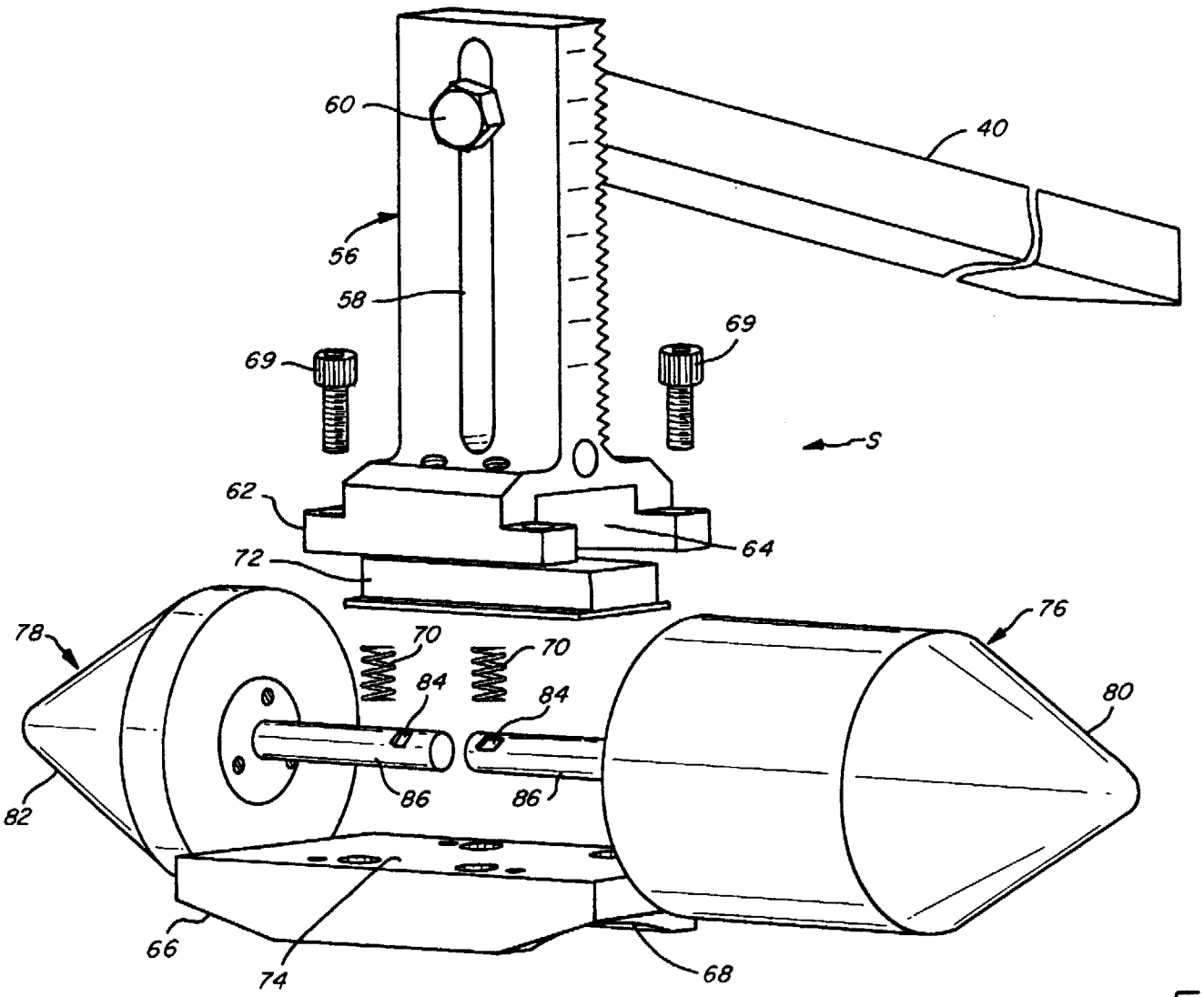
FIG. 4 is a detail of the mounting of the sensor and rollers shown in FIG. 1.

The ultrasonic sensors and the way they are mounted to drum 12 can best be seen by looking at FIGS. 1 and 2. Extending from drum 12 is a plurality of brackets 24, 26, 28 and 30. These brackets are stationary with respect to drum 12. The brackets 24, 26, 28 and 30 have, respectively, pivot points 32, 34, 36, and 38. Connected to each pivot point, respectively, are links 40, 42, 44, and 46. Links 40–46 are pivotally mounted and hold a sensor assembly S, as shown in FIG. 4. Links 40–46 are, respectively, biased due to springs 48, 50, 52 and 54. Springs 48–54 bias the sensor assembly S toward the pipe P. The illustration in FIG. 4 is typical for all of the sensor mountings and the description of sensor assembly S is applicable to as many sensor assemblies as are used. Those skilled in the art will appreciate that the number of sensor assemblies is optional depending upon the design requirements. The initial orientation of sensor assembly S is controlled by the place of attachment between a link such as 40 and a support 56. The support 56 has an elongated slot 58 which allows adjustable connection between support 56 and link 40 by selective tightening of bolt 60. Bolt 60 extends through slot 58 and engages link 40. Upon tightening, the spatial relationship between link 40 and support 56 is established.

At the lower end of support 56 is a mounting flange 62. Within mounting flange 62 is a recess 64 that accepts the ultrasonic sensor. The sensor is preferably attached to the glide plate 66. Glide plate 66 is floatingly mounted to flange 62. Glide plate 66 has a curved underside 68, which rides on the outer surface of the pipe P. Bolts 69 pass through flange 62, through spring 70, and into glide plate 66 to *secure the flange to the guide plate. Springs 70* provide a biasing force onto glide plate 66 to keep it flush against pipe P and to allow it to float with pipe roundness imperfections so that good contact is continuously maintained.

The sensor assembly S also includes a lead roller 76 and a tail roller 78. Each of the rollers 76 and 78 has a conical surface 80 and 82, respectively. The conical surface 80 is normally in the lead position, as shown in FIG. 1. As the pipe P advances and bumps into cones 80, the sensor assembly S is displaced radially outwardly against the force of springs 48–54. Further advance of the pipe P brings its outer surface in contact with curved surface 68. Rollers 76 and 78 are secured to support 56 through openings 84 on extension shafts 86, which extend from the rollers 76 and 78. In this manner sensor assembly S is biased toward pipe P so that the cylindrical portions of rollers 76 and 78 ride on pipe P.

In order to obtain meaningful readings, the outer surface of pipe P is made wet prior to its contact with floating curved surface 68. To accomplish this, a water supply shown generally as 88 is connected to one or more nozzles 90 to feed a liquid such as water onto the outer surface of pipe P as it advances toward opening 22. Since the drum 12 rotates and rollers 76 are in contact with the outer surface of pipe P, the applied liquid from nozzle 90 is "painted" over the outer surface of the pipe in a continuous manner so as to effectively provide a coating on the surface of pipe P to facilitate accurate readings. The coned surface 82 is provided in tail roller 78 in the event the direction of the pipe needs to be reversed after it has passed through the apparatus A to facilitate the examination of the pipe in the opposite direction. If a reverse of direction is required, the end of the pipe then encounters cone 82, which repositions the sensor assembly S appropriately so that curved surface 68 will come in contact with the outer surface of pipe P.

Referring now to FIG. 2, it is seen that the sensor assembly S is connected to plate 92, which is part or drum 12. On the opposite end of drum 12 is another plate 94, to which is mounted a signal processor. The signal processor 96 is a computer device to analyze the signals received from the sensors 72 and is conventional. What is not conventional is that the signal processor or computer 96 is mounted to plate 94. Those skilled in the art will appreciate that the computer 96 rotates with the same speed as the sensor assemblies S. Since the computer 96 is rotated with the sensors 72, each sensor 72 can be hardwired to the computer 96. The output signal from the computer 96 goes back through plate 94 and to a slip ring assembly 98 located between plates 92 and 94. The output signal from the computer 96 is then taken off of the apparatus A where it can be connected to conventional display equipment for visual observation and recordation of any flaws detected in the pipe P.

To keep the computer 96 from being contaminated by the applied liquid and from the local environment, a housing 100 is provided over plate 94. Access for visual inspection and/or calibration of the computer 96 is provided through a door 102. Door 102 can be used to actuate a switch (not shown) which prevents the operation of motor 14 when door 102 is in the open position. This is a safety feature which prevents accidents and/or damage to the equipment.

Mounted below plates 92 and 94 is at least one catch pan 104, which collects the Liquid or water applied to the pipe P by nozzles 90. As shown in FIG. 2, pan 104 is fairly lengthy and extends back toward the belt 16. Additionally, for housekeeping a gas spray assembly 106 is connected to a gas source (not shown) to blow back any liquid that still remains on the outer surface of pipe P at the outlet end of the apparatus A. The spray nozzles 106 blow the liquid back along pipe P until it can fall down into another pan 104 and into drainpipe 108 (see FIG. 2).

Those skilled in the art will appreciate that the speed that the drum 12 and the sensor assembly S are driven can be regulated to a desired level. By a proper combination of linear speed of the pipe P and rotational speed of the sensor assembly S, the entire pipe surface can be covered. In fact, the combination of linear speed of pipe P and rotational speed of sensors S can be arranged so that there is overlapping testing of the outer surface of pipe P.

One of the distinct advantages of the apparatus A as illustrated is its compact design and its economical construction. As such it can be added as an item in line with existing electromagnetic and gamma ray testing machines. Since it has such a narrow profile it may not require extensive revisions to the production line to retrofit the apparatus or the present invention.

The use of the computer 96 mounted on the drum eliminates one of the nagging problems of prior designs. This problem is that prior designs use a stationary computer requiring a slip ring connection between the output of the sensors 72 and the computer 96. Since the output signal from the sensors 72 is a high-frequency, low-voltage signal, electrical interference was a problem with past designs at the point where the slip ring was located. In the apparatus A of the present invention, there is no slip ring between the sensors 72 and the computer 96. That is a hardwired connection. Instead, the output of computer 96 goes through slip ring 98. Since the computer signal on the output side is low-frequency and high-voltage, it is less susceptible to interference when the signal passes through a slip ring 98.

The use of the sprays 90, in combination with the rollers 76, facilitates the application of a continuous liquid coating to ensure accurate measurements without any dry spots at the point of test.

Another advantage of the apparatus of the present invention is the flexible mounting of sensors 72. Springs 70 bias the glide plate 66 against the pipe P to ensure continuous contact and accurate readings. The apparatus A is adjustable to handle numerous pipe sizes through the spring mounting and the details illustrated in FIG. 4. The apparatus A is also much more economical to construct and install, both from the point of view of space and connection of utilities.

The use of the apparatus can now make it possible for pipe customers to have a 100 percent wall inspection for flaws of the entire length of a pipe P more economically than a complicated ultrasonic tester having a multiplicity of stationary sensors oriented in different directions and the advancing pipe rotating over such stationary sensors. While the apparatus A provides no greater accuracy in ultrasonic testing than the multi-sensored stationary testing devices, it does provide similar level of quality inspection for considerably less cost.

Depending on the application, a different number of sensors 72 can be used from the four shown in the figures. While the preferred embodiment has been illustrated as the best way to flex mount the sensors 72, other additional ways to provide flexible or floating mounting are also within the purview of the invention.

The foregoing disclosure and description of the invention are illustrative and explanatory thereof, and various changes in the size, shape and materials, as well as in the details of the illustrated construction, may be made without departing from the spirit of the invention.

I claim:

1. An apparatus for testing tubular goods, comprising:

(a) a frame;

(b) sensing means mounted to said frame for detecting flaws in a tubular and for sending an output signal, said sensing means comprising at least one ultrasonic sensor, a movably mounted holder for said ultrasonic sensor, and a shoe mounted to said holder;

(c) computing means on said frame hardwired to said sensing means to process said output signal of said sensing means and deliver a second output signal;

(d) means for rotating said sensing means and computing means in tandem on said frame;

(e) means on said frame for allowing a takeoff of said second signal and for supplying power as said sensing means and computing means are rotated, said means for allowing a takeoff of said second signal and for supplying power comprising a slip ring assembly;

(f) a tubular to be inspected, said tubular being centrally located on said frame such that said means for rotating can rotate said sensing means and said computing means around the outer surface of said tubular;

(g) at least one fluid outlet directed at the outer surface of said tubular; and (h) a lead roller mounted to said holder.

2. The apparatus of claim 1, wherein said lead roller has a tapered end adapted to engage the tubular for displacement or said roller and sad holder.

3. The apparatus of claim 2, further comprising:

(a) a biasing means mounted on said frame capable of driving said shoe toward the tubular; and (b) a tail roller mounted to said holder on the opposite side of said shoe from said lead roller, said tail roller having an oppositely oriented tapered surface to said lead roller.

4. The apparatus of claim 3, further comprising:

(a) drying means for displacing fluid applied by said outlet, off the tubular; and (b) collection means for gathering [any] fluid displaced by said drying means off the tubular.

5. The apparatus of claim 4, wherein:

said drying means comprises at least one gas nozzle; and said collection means comprises a drain pan under the tubular to catch liquid blown off the tubular by said gas nozzle.

6. The apparatus of claim 5, wherein:

said means for rotating drives said sensor at a speed sufficient to obtain at least 100 percent coverage of the outer surface of the tubular.

7. An apparatus for testing tubular goods, comprising:

(a) a frame;

(b) a shoe floatingly mounted on said frame;

(c) a support drum mounted on said frame;

(d) at least one sensor mounted to said shoe;

(e) a computing means hardwired to said sensor for processing a signal from said sensor, said computing means and sensor means mounted to said frame for tandem movement; and (f) a tubular to be inspected, insertable through the center of said support drum such that said computing means and sensor can rotate in tandem around the outer surface of said tubular;

(g) at least one fluid outlet directed at the tubular, (h) applicator means to spread fluid deposited [in] *on* the tubular by said outlet; and (i) a lead roller mounted to said shoe.

8. The apparatus of claim 7, wherein said lead roller has a tapered end adapted to engage the tubular for displacement of said roller and said holder.

9. The apparatus of claim 8, further comprising:

(a) a biasing means mounted on said frame capable of driving said shoe toward the tubular; and (b) a tail roller mounted to said holder on the opposite side of said shoe from said lead roller, said tail roller having an oppositely oriented tapered surface to said lead roller.

10. The apparatus of claim 9, further comprising:

(a) drying means for displacing fluid applied by said outlet, off the tubular; and (b) collection means for gathering [any] liquid displaced by said drying means off the tubular.

11. The apparatus of claim 10, wherein:

said drying means comprises at least one gas nozzle; and said collection means comprises a drain pan under the tubular to catch liquid blown off the tubular by said gas nozzle.

12. An apparatus for testing tubular goods, comprising:

(a) a frame;

(b) at least one ultrasonic sensor mounted to said frame;

(c) a computing means hardwired to said sensor for processing a signal from said sensor;

(d) a movably mounted holder housing said ultrasonic sensor;

(e) a shoe floatingly mounted on said holder;

(f) means for rotating said ultrasonic sensor and said computing means in tandem on said frame;

(g) means on said frame to allow a takeoff of the signal from said computing means and to supply power as said sensor and computing means are rotated;

(h) coating means on said frame, [further comprising:] *including*

[(i)] at least one fluid outlet directed at a tubular[;] and *at least one lead roller mounted to said holder and having a tapered end, the lead roller spreading*

[(j) applicator means to spread] fluid deposited on a tubular by said *at least one* outlet [said applicator means comprising at least one lead roller mounted to said holder, said lead roller having a tapered end].

*13. Apparatus for inspecting a plurality of elongate tubulars, comprising:*

*an inspection machine frame;*

*a drum spaced radially outward from a respective tubular, the drum being rotatable about a central axis with respect to the frame;*

*a motor for rotating the drum;*

*a plurality of sensors each mounted circumferentially about the rotatable drum for detecting flaws in each tubular and for outputting electrical sensed signals;*

*an electronic processor fixedly mounted on the drum at a position axially opposite the plurality of sensors with respect to a slip ring assembly and electrically interconnected with each of the plurality of sensors to process the electrical sensed signals from each of the plurality of sensors and for delivering processed signals representing flaws in the tubular;*

*the slip ring assembly secured to the frame for transmitting the processed signals from the electronic processor;*

*a liquid outlet directed at an outer surface of the tubular for wetting a radial spacing between each of the plurality of sensors and the tubular; and*

*a housing at least substantially enclosing the electronic processor for protecting the processor from the liquid discharged from the liquid outlet.*

*14. The apparatus as defined in claim 13, further comprising:*

*a liquid storage supply for supplying liquid to the liquid outlet; and*

*the liquid outlet being spaced axially opposite the electronic processor with respect to the slip ring assembly and including at least one nozzle for selectively discharging the liquid onto the surface of the tubular.*

*15. The apparatus as defined in claim 14, further comprising:*

*a hood for at least partially containing the liquid discharged from the at least one nozzle onto the tubular; and*

*a drain pan positioned below the drum to catch the liquid discharged from the at least one nozzle onto the tubular.*

*16. The apparatus as defined in claim 14, further comprising:*

*at least one gas nozzle for discharging a drying gas onto the tubular.*

*17. The apparatus as defined in claim 13, further comprising:*

*an access door within the housing for selectively accessing the processor.*

*18. The apparatus as defined in claim 13, further comprising:*

*a curved underside concave planar surface adjacent each of the plurality of sensors and rotatable therewith with respect to the frame, each curved underside planar surface geometrically conforming substantially to an exterior cylindrical surface of the tubular for coating a radial spacing between the respective sensor and the tubular with the discharged liquid.*

*19. The apparatus as defined in claim 18, further comprising:*

*each of the plurality of sensors is an ultrasonic sensor; and*

*a plurality of biasing members each for biasing at least one of the plurality of ultrasonic sensors toward the tubular.*

*20. The apparatus as defined in claim 13, wherein each of the plurality of sensors is hardwired to the electronic processor.*

*21. The apparatus as defined in claim 13, further comprising:*

*a plurality of sensor supports each for movably mounting a respective sensor on the drum.*

*22. The apparatus as defined in claim 13, further comprising:*

*the plurality of sensors include at least four ultrasonic spaced circumferentially about the rotatable drum; and*

*the motor rotates the drum at a speed such that the at least four ultrasonic sensors obtain at least 100% coverage at an outer surface of the tubular.*

*23. The apparatus as defined in claim 13, further comprising:*

*a displacement mechanism for moving each of the plurality of sensors radially with respect to varying diameters of the plurality of elongate tubulars.*

*24. Apparatus for inspecting a plurality of elongate tubulars, comprising:*

*an inspection machine;*

*a drum spaced radially outward from a respective tubular, the drum being rotatable about a central axis with respect to the frame;*

*a motor for rotating the drum;*

*a plurality of ultrasonic sensors each mounted circumferentially about the rotatable drum for detecting flaws in the supported tubular and for outputting sensed signals;*

*a slip ring assembly secured to the frame for transmitting radially outward therethrough indications of the sensed signals;*

*a liquid storage supply for supplying liquid;*

*at least one nozzle selectively positioned at a stationery location with respect to said frame for discharging the liquid onto the surface of the tubular at a position spaced axially from the plurality of sensors for wetting a radial spacing between each of the plurality of sensors and the tubular; and*

*a curved underside concave planar surface adjacent each of the plurality of sensors and rotatable therewith with respect to the frame, each curved underside planar surface geometrically conforming substantially to an exterior cylindrical surface of the tubular for coating a radial spacing between a respective sensor and the tubular with the discharged liquid.*

*25. The apparatus as defined in claim 24, further comprising:*

*a hood for at least partially containing the liquid discharged from the at least one nozzle onto the tubular; and*

*a drain pan positioned below the drum to catch the liquid discharged from the at least one nozzle onto the tubular.*

*26. The apparatus as defined in claim 24, further comprising:*

*at least one gas nozzle for discharging a drying gas onto the tubular.*

*27. The apparatus as defined in claim 24, further comprising:*

*an electronic processor mounted on the drum at a preselected circumferential location and electrically interconnected with each of the plurality of sensors to process the sensed signals from each of the plurality of sensors and for delivering processed signals representing flaws in the tubular;*

*a housing for at least substantially enclosing the electronic processor to protect the processor from the discharged liquid; and*

*an access door within the housing for selectively accessing the processor.*

*28. The apparatus as defined in claim 25, further comprising:*

*each of the plurality of sensors is an ultrasonic sensor;*

*a plurality of biasing members each for biasing at least one of the plurality of ultrasonic sensors toward the tubular; and*

*a plurality of sensor supports each for movably mounting a respective ultrasonic sensor on the drum.*

*29. The apparatus as defined in claim 25, further comprising:*

*the plurality of sensors includes at least four ultrasonic sensors spaced circumferentially about the rotatable drum; and*

*the motor rotates the drum at a speed such that the at least four ultrasonic sensors obtain at least 100% coverage at an outer surface of the tubular.*

*30. A method of inspecting a plurality of elongate tubulars, comprising:*

*successively supporting each of the plurality of elongate tubulars relative to an inspection machine frame;*

*positioning each supported tubular within a drum spaced radially outward from the supported tubular;*

*mounting a plurality of sensors circumferentially about the drum;*

*securing a slip ring assembly to the frame to receive electrical signals from the plurality of sensors;*

*mounting an electronic processor on the drum at a position axially opposite the plurality of sensors with respect to the slip ring assembly;*

*electrically interconnecting each of the plurality of sensors to the electronic processor to process the sensed signals from each of the plurality of sensors and deliver processed signals representing flaws in the supported tubular;*

*rotating the drum with respect to the frame and the supported tubular;*

*directing a liquid from a location stationary with respect to the frame onto an outer surface of the supported tubular spaced axially from the plurality of sensors for wetting a spacing between each of the plurality of sensors and the supported tubular;*

*transmitting the processed signals from the electronic processor through the slip ring assembly secured to the frame; and*

*detecting flaws in the supported tubular based on the transmitted signals.*

*31. The method as defined in claim 30, further comprising:*

*containing the liquid discharged from the at least one nozzle onto the supported tubular with a hood; and*

*positioning a drain pan below the drum to catch the liquid discharged from the at least one nozzle onto the supported tubular.*

*32. The method as defined in claim 30, further comprising:*

*discharging a drying gas onto the supported tubular.*

*33. The method as defined in claim 30, further comprising:*

*at least substantially enclosing the electronic processor with a housing to protect the processor from the discharged liquid; and*

*selectively accessing the processor through an access door within the housing.*

*34. The method as defined in claim 30, further comprising:*

*biasing each of the plurality of sensors toward the supported tubular; and*

*displaying the transmitted signals to detect flaws in each of the supported tubulars.*

*35. The method as defined in claim 30, further comprising:*

*movably mounting each of the plurality of sensors on the rotatable drum.*

*36. A method of inspecting a plurality of elongate tubulars,*

*successively supporting each of the plurality of elongate tubulars relative to an inspection machine frame;*

*positioning each supported tubular within a drum spaced radially outward from the supported tubular;*

*mounting a plurality of sensors circumferentially about the drum;*

*rotating the drum with respect to the frame and the supported tubular;*

*directing a liquid from a location stationary with respect to the frame onto an outer surface of the supported tubular spaced axially from the plurality of sensors for wetting a spacing between each of the plurality of sensors and the supported tubular;*

*providing a curved underside concave planar surface adjacent each of the plurality of sensors and rotatable therewith for geometrically conforming substantially to an exterior cylindrical surface of the supported tubular and coating a radial spacing between the respective sensor and the supported tubular with the discharged liquid;*

*transmitting the processed signals from the rotating drum to a receiver secured to the frame; and*

*using the transmitted signals to detect flaws in the supported tubular.*

*37. The method as defined in claim 36, further comprising:*

*partially containing the liquid discharged from the at least one nozzle onto the supported tubular with a hood; and*

*positioning a drain pan below the drum to catch the liquid discharged from the at least one nozzle onto the supported tubular.*

*38. The method as defined in claim 36, further comprising:*

*discharging a drying gas onto the supported tubular.*

*39. The method as defined in claim 36, further comprising:*

*securing a slip ring assembly for the frame to receive electrical signals from the plurality of sensors.*

*40. The method as defined in claim 39, further comprising:*

*mounting an electronic processor on the drum at a preselected circumferential location; and*

*electrically interconnecting each of the plurality of sensors to the electronic processor to process the sensed signals from each of the plurality of sensors and delivering processed signals representing flaws in the supported tubular.*

*41. The method as defined in claim 40, further comprising:*

*at least substantially enclosing the electronic processor in a housing to protect the processor from the discharged liquid; and*

*selectively accessing the processor through an access floor within the housing.*

*42. The method as defined in claim 36, further comprising:*

*biasing each of the plurality of sensors toward the supported tubular.*

*43. The method as defined in claim 36, further comprising:*

*movably mounting each of the plurality of sensors on the drum.*

* * * * *

UNITED STATES PATENT AND TRADEMARK OFFICE

CERTIFICATE OF CORRECTION

PATENT NO. : RE 36,130
DATED : March 9, 1999
INVENTOR(S) : John Haynes

It is certified that error appears in the above-identified patent and that said Letters Patent is hereby corrected as shown below:

Column 8,
Line 17, add -- sensors -- after "ultrasonic".
Line 30, add -- frame -- after "inspection machine".

Column 10,
Line 23, add -- comprising: -- after "tubulars,".
Line 44, delete "the processed" before "signals".

Signed and Sealed this

Tenth Day of September, 2002

*Attest:*

*Attesting Officer*

JAMES E. ROGAN
*Director of the United States Patent and Trademark Office*